US006304626B1

United States Patent
Adachi et al.

(10) Patent No.: US 6,304,626 B1
(45) Date of Patent: Oct. 16, 2001

(54) TWO-DIMENSIONAL ARRAY TYPE OF X-RAY DETECTOR AND COMPUTERIZED TOMOGRAPHY APPARATUS

(75) Inventors: Akira Adachi, Otawara; Kenji Igarashi, Yokohama, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/420,944

(22) Filed: Oct. 19, 1999

(30) Foreign Application Priority Data

Oct. 20, 1998 (JP) .................................................. 10-298641

(51) Int. Cl.[7] .................................................. G01N 23/00
(52) U.S. Cl. .................................................. 378/19; 378/4
(58) Field of Search .................................. 378/19, 12, 13, 378/21, 146, 147, 149, 4, 154, 155

(56) References Cited

U.S. PATENT DOCUMENTS

| 4,731,534 | * | 3/1988 | Klein et al. | 250/366 |
| 4,982,096 | * | 1/1991 | Fujii et al. | 250/367 |
| 5,131,021 | * | 7/1992 | Gard et al. | 378/19 |
| 5,400,378 | * | 3/1995 | Pfoh et al. | 378/19 |
| 5,510,622 | * | 4/1996 | Hu et al. | 250/367 |
| 5,666,395 | * | 9/1997 | Tsukamoto et al. | 378/98.4 |
| 6,018,566 | * | 1/2000 | Eberhard et al. | 378/154 |
| 6,091,795 | * | 7/2000 | Schafer et al. | 378/19 |

FOREIGN PATENT DOCUMENTS

| 356054076 A | * | 5/1981 | (JP) . |
| 5-184563 | | 7/1993 | (JP) . |
| 9-005444 | | 1/1997 | (JP) . |
| 1107622 A | * | 3/1999 | (JP) . |

* cited by examiner

Primary Examiner—Robert H. Kim
Assistant Examiner—Irakli Kiknadze
(74) Attorney, Agent, or Firm—Oblon, Spivak, McClelland, Maier & Neustadt, P.C.

(57) ABSTRACT

A two-dimensional array type of X-ray detector, incorporated into an X-ray computerized tomography apparatus, has a plurality of X-ray detecting elements arranged in the X and Y directions for detecting incident X-rays into electric signals. A mask is placed on the X-ray incidence side of the X-ray detecting elements. The mask is formed with a pattern of shield portions in line form each extending substantially parallel to the channel direction (X direction) to shield edges of all the X-ray detecting elements arranged in the x direction from incident X-rays. Thereby, the instability of sensitivity of X-ray detection of the edges of the X-ray detecting elements and arrangement errors of the X-ray detecting elements in the slice direction (Y direction) are canceled out.

22 Claims, 6 Drawing Sheets

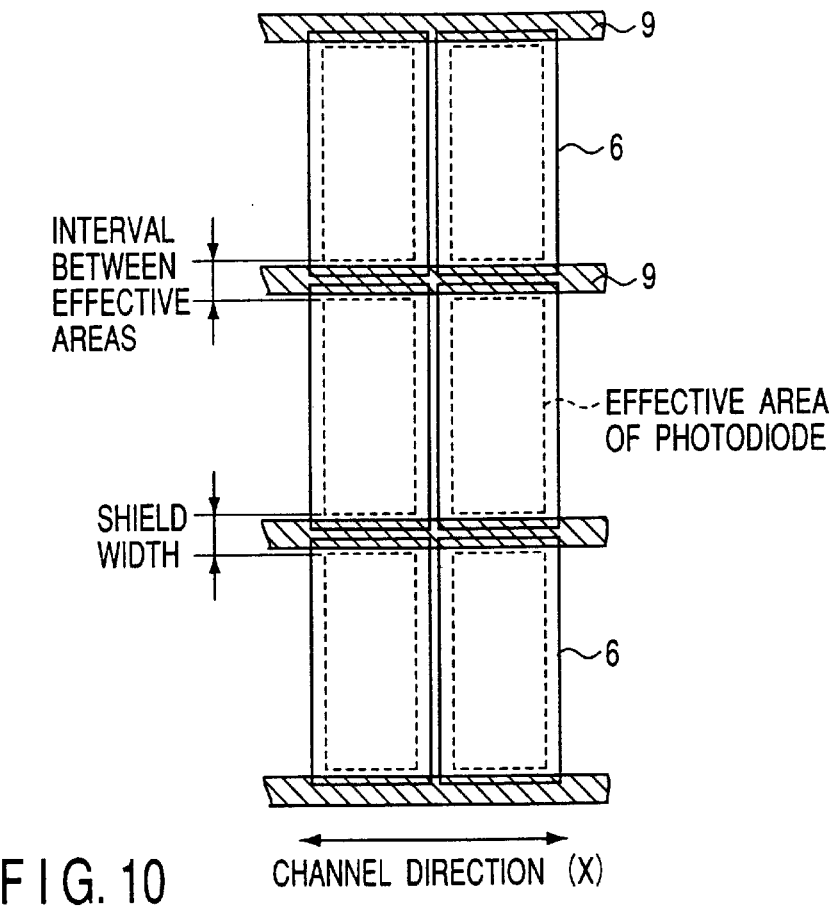
FIG. 10
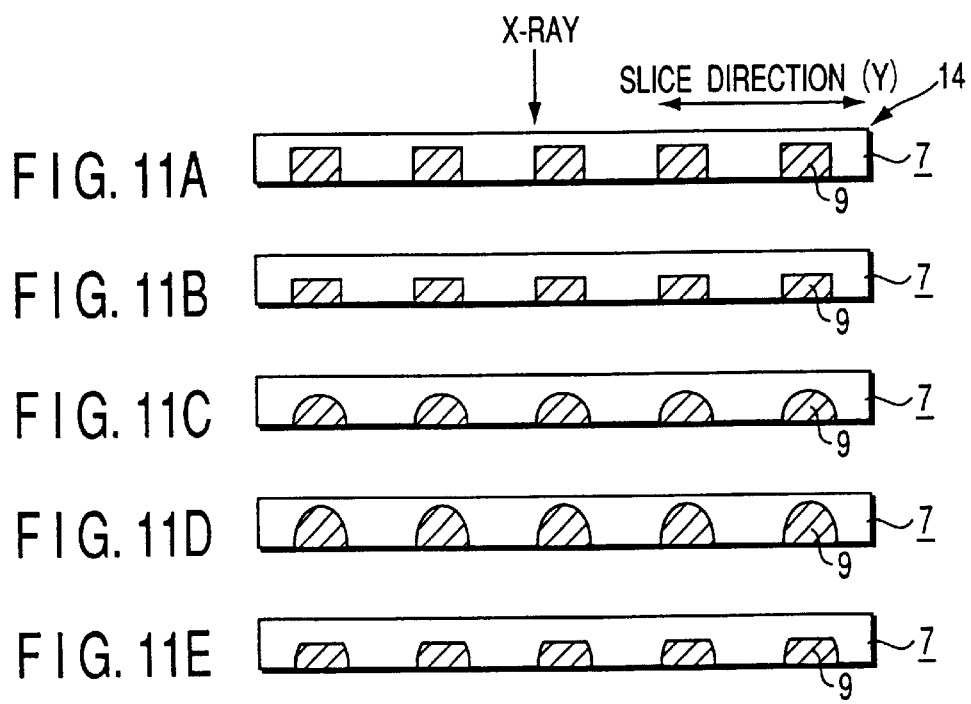
FIG. 11A
FIG. 11B
FIG. 11C
FIG. 11D
FIG. 11E

TWO-DIMENSIONAL ARRAY TYPE OF X-RAY DETECTOR AND COMPUTERIZED TOMOGRAPHY APPARATUS

BACKGROUND OF THE INVENTION

The present invention relates to a two-dimensional array type of X-ray detector and a computerized tomography apparatus equipped with that X-ray detector.

The principal scan scheme in current X-ray computerized tomography apparatuses is the so-called third-generation type which collects projection data repeatedly while an X-ray tube and an X-ray detector revolve around a living body under examination. The principal X-ray detector is the so-called one-dimensional type in which a number of X-ray detecting elements are arranged in the channel direction.

In recent years, a scintillation type of X-ray detecting element has been put into practical use which consists of a combination of a scintillator and a photodiode. Having a good X-ray-to-electricity conversion efficiency and being compact and light, this type of detecting element surpasses an ionization chamber type of detector.

This compact, light X-ray detecting element has contributed greatly to the practical use of a two-dimensional array type of X-ray detector (also referred to as the multislice type of X-ray detector) in which a plurality of X-ray detecting elements are arrayed into a matrix. The two-dimensional array X-ray detector is manufactured roughly in two stages as shown in FIG. 1: in the first stage, a plurality of X-ray detecting elements corresponding in number to slices, for example, three X-ray detecting elements are arrayed along the Y direction (slice direction) to produce a module and, in the second stage, a plurality of modules corresponding in number to channels are arranged along the x direction (channel direction) so as to form a circular arc.

Here, a problem is that a module arrangement error arises in the second stage. That is, the X-ray detecting elements cannot be arranged accurately in a line in the channel direction. As a result, an artifact may be produced on a reconstructed image.

In addition, the scintillation type of X-ray detecting element has a property that the sensitivity drops abruptly in the vicinity of the edges of the scintillator as shown in FIG. 2 because the effective area of the photodiode is smaller than the plane of X-ray incidence of the scintillator. The half shadow of the collimator falls mainly on the edge portions of the scintillator. The half shadow greatly varies with variations in the geometrical position relationship of a collimator with the X-ray tube and/or the detector due to thermal expansion of parts of the X-ray tube. Thus, the sensitivity at the edges is very unstable, which may produce an artifact on the reconstructed image.

A method to solve the above problem is disclosed in Japanese Unexamined Patent Publication No. 5-184563. According to this method, a plurality of collimators are arranged at regular intervals along the slice direction between a body under examination and a two-dimensional X-ray detector. The collimator allows X-rays to be formed smaller than the dimension of the effective area of each X-ray detecting element in the slice direction. The resulting X-rays fall on only a portion 100 in the vicinity of the center of the effective area of each X-ray detecting element as shown in FIG. 1, thus allowing the effective area of the X-ray detecting element to have a margin. The module arrangement error is therefore allowed by the amount corresponding to that margin.

In Japanese Unexamined Patent Publication No. 9-224929, a collimator that is adjustable during scanning, called a dynamic pre-patient collimator, is provided between an X-ray tube and a body under examination, which allows the position of X-ray exposure to shift so as to reduce the effect of module arrangement errors.

However, the above-described two methods are accompanied by two problems that the half shadow is produced by the collimator and errors of collimator arrangement with respect to the X-ray tube and the X-ray detector are unavoidable. This means that the cause of the artifact is only changed from the module arrangement error to the two problems.

BRIEF SUMMARY OF THE INVENTION

It is an object of the present invention to provide a two-dimensional array type of X-ray detector which cancels out the instability of sensitivity of X-ray detection of the edges of the X-ray detecting elements and arrangement errors of X-ray detecting element modules.

A two-dimensional array type of X-ray detector of the present invention, incorporated into an X-ray computerized tomography apparatus, has a plurality of X-ray detecting elements arranged in the x and Y directions for detecting incident X-rays into electric signals. A mask is placed adjacent to the X-ray detecting elements in the X-ray incidence side. The mask is formed with a pattern of shield portions in line form each extending substantially parallel to the channel direction (X direction) to shield edges of all the X-ray detecting elements arranged in the X direction from incident X-rays. Thereby, the instability of sensitivity of X-ray detection of the edges of the X-ray detecting elements and arrangement errors of the X-ray detecting elements in the slice direction (Y direction) are canceled out.

Another two-dimensional array type of X-ray detector of the present invention, incorporated into an X-ray computerized tomography apparatus, has a plurality of X-ray detecting elements arranged in the X and Y directions for detecting incident X-rays into electric signals. A mask is placed adjacent to the X-ray detecting elements in the X-ray incidence side. The mask has a plurality of shield portions and a transparent portion substantially transparent to X-rays for supporting the shield portions. The shield portions are patterned in lines substantially parallel to the X direction. The edges of all the X-ray detecting elements arranged in the channel direction (X direction) are shielded from incident X-rays. Thereby, the instability of sensitivity of X-ray detection of the edges of the X-ray detecting elements and arrangement errors of the X-ray detecting elements in the slice direction (Y direction) are canceled out.

Still another two-dimensional array type of X-ray detector of the present invention, incorporated into an X-ray computerized tomography apparatus, has a plurality of X-ray detecting elements arranged in the X and Y directions for detecting incident X-rays into electric signals. A mask is placed adjacent to the X-ray detecting elements in the X-ray incidence side. The mask shields the edges of each X-ray detecting element which are opposed to each other in the Y direction from incident X-rays. Thereby, the instability of sensitivity of X-ray detection of the edges of each X-ray detecting element is canceled out.

A further two-dimensional array type of X-ray detector of the present invention, incorporated into an X-ray computerized tomography apparatus, has a plurality of X-ray detecting elements arranged in the X and Y directions for detecting incident X-rays into electric signals. A mask is placed adjacent to the X-ray detecting elements in the X-ray incidence side. The mask has a plurality of shield portions for shielding the edges of each X-ray detecting element which are opposed to each other in the Y direction from incident X-rays and a transparent portion substantially transparent to X-rays for supporting the shield portions. Thereby, the instability of sensitivity of X-ray detection of the edges of the X-ray detecting elements is canceled out.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 10 illustrates the width of the shield portions of the mask of the present invention; and FIGS. 11A through 11E show variations of cross-sectional shapes of the shield portions of the mask of the present invention.

DETAILED DESCRIPTION OF THE INVENTION

Hereinafter, a two-dimensional array type X-ray detector and computerized tomography apparatus of the invention will be described in terms of their preferred embodiments with reference to the accompanying drawings.

Figure 1:
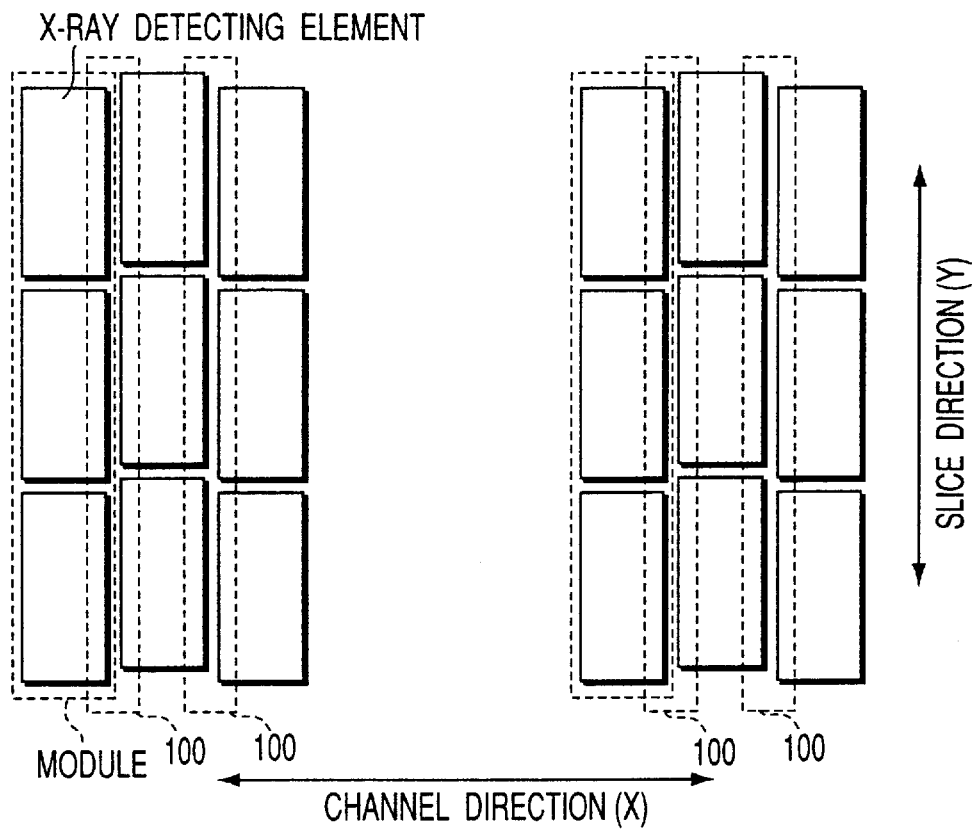
FIG. 1 illustrates arrangement errors of conventional X-ray detecting elements.
Figure 2:
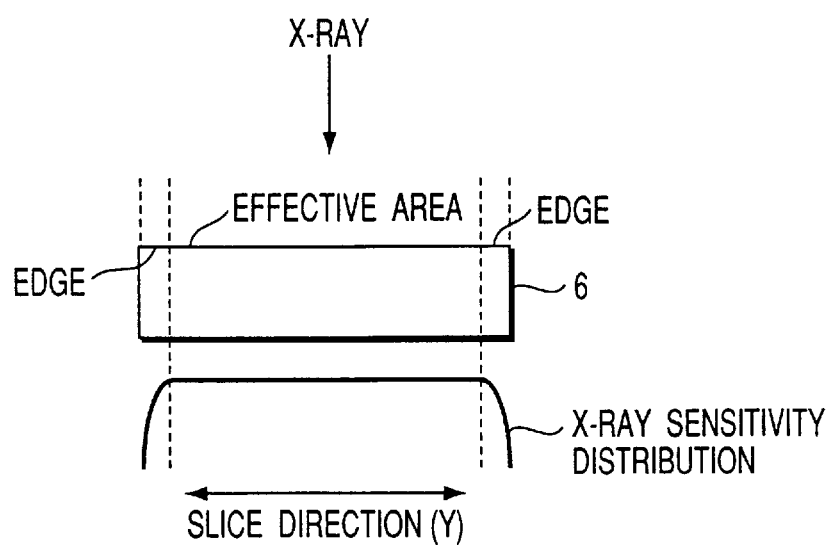
FIG. 2 shows the X-ray detection sensitivity of conventional X-ray detecting elements.
Figure 3:
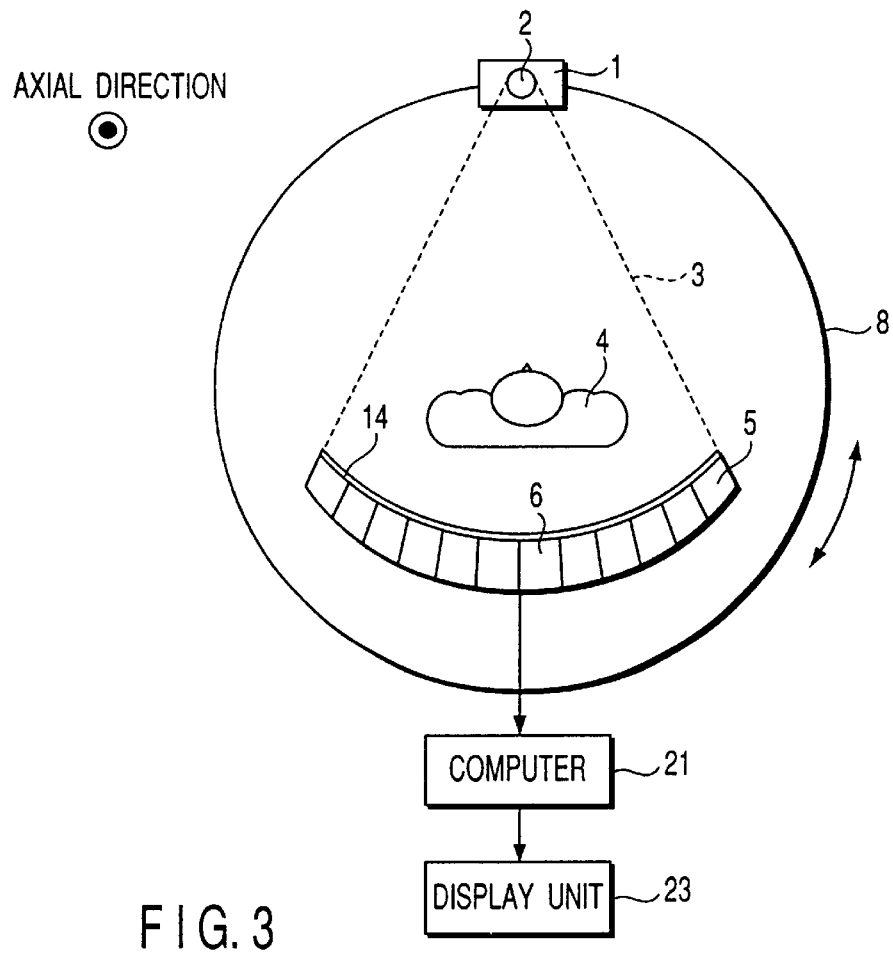
FIG. 3 shows schematically the internal structure of the gantry in an X-ray computerized tomography apparatus of an embodiment of the invention.

FIG. 3 schematically illustrates the internal structure of the gantry of computerized tomography apparatus. Reference numeral 8 denotes a ring that is rotatable. To the ring are mounted an X-ray tube 1 and a two-dimensional array X-ray detector 5 so that they are opposed to each other with a human body 4 under examination interposed therebetween. X-rays 3 emitted in the shape of a fan from a focus spot 2 of the X-ray tube 1 pass through the human body 4 and are then detected by the X-ray detector 5. A computer 21 produces tomography image data concerning at least one slice on the basis of data (projection data) detected by the X-ray detector 5. A display unit 23 displays a tomography image based on the tomography image data.

Figure 4:
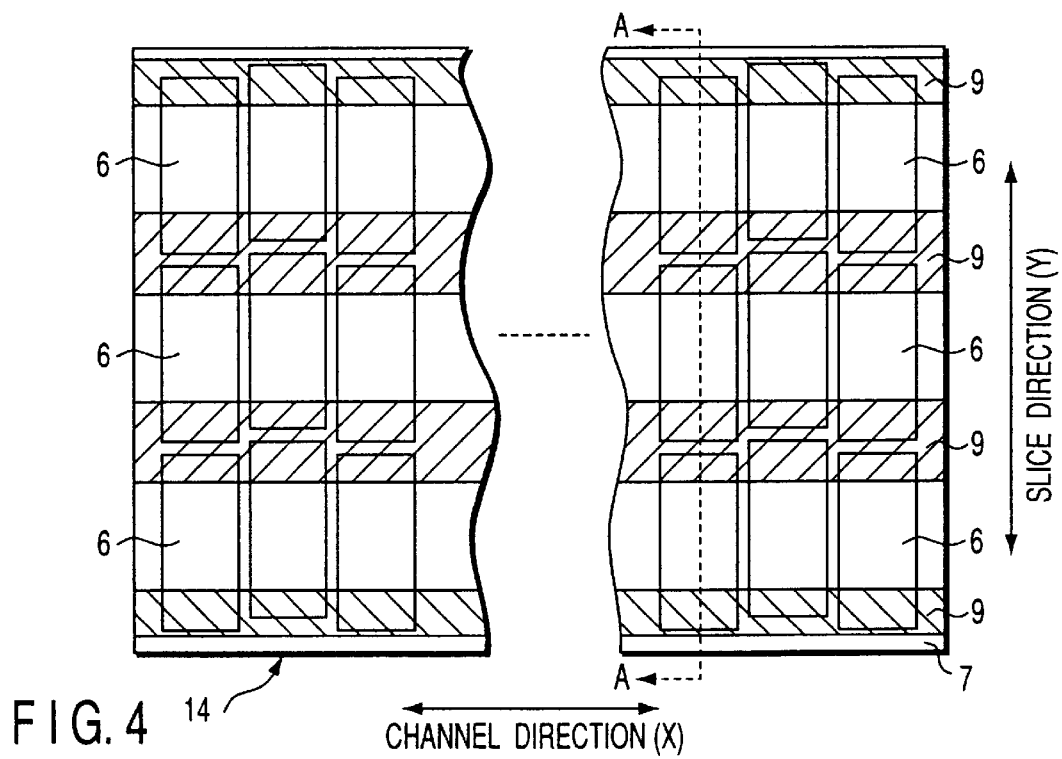
FIG. 4 is a plan view of the two-dimensional array type of X-ray detector shown in FIG. 3.
Figure 5:
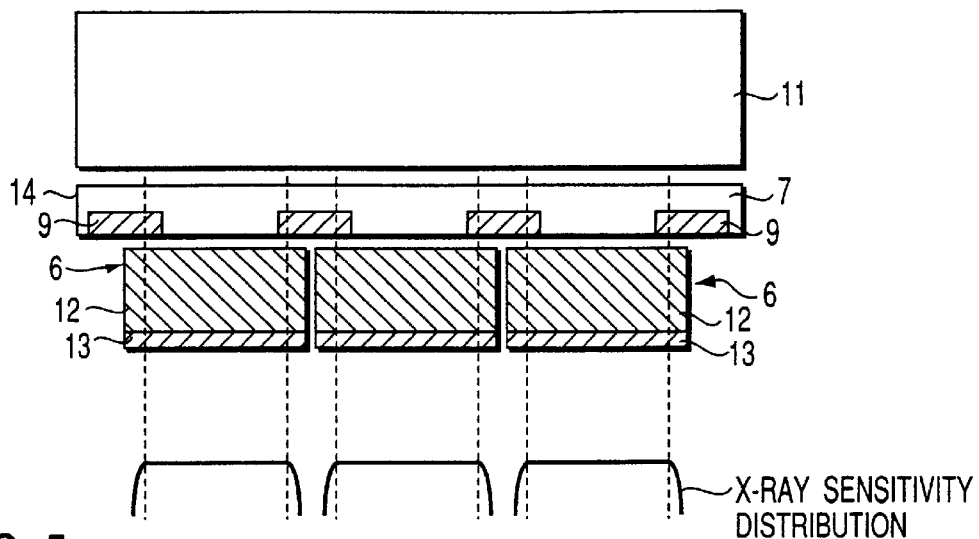
FIG. 5 is a cross-sectional view taken along line A—A in FIG. 4.

FIG. 4 is a plan view of the two-dimensional x-ray detector 5. A plurality of X-ray detecting elements 6, each consisting of, for example, a scintillator 12 and a photodiode 13, are arrayed in a matrix in the X direction (channel direction) and the Y direction (slice direction). In practice, in the channel direction, the X-ray detecting elements 5 are arranged not in a linear fashion but in the shape of circular arc with the distance from the X-ray focus 2 as radius. On the X-ray incidence side of the X-ray detecting elements 6 is placed a collimator 11. A mask 14 is placed between the X-ray detecting elements 6 and the collimator 11.

The mask 14 is formed in the shape of a plate that is somewhat curved along the channel direction to conform to the arc shape of the array of the X-ray detecting elements. The mask is formed such that a plurality of shield portions 9 that are not transparent to X-rays are supported by a transparent portion 7 substantially transparent to X-rays. The X-ray adsorption coefficient is zero or zero approximate value. The shield portions are each formed in the shape of a line that extends along the channel direction and are arranged in the slice direction at a pitch equal to the pitch (center-to-center distance) of the X-ray detecting elements 6 in the slice direction. The mask 14 is aligned with the array of X-ray detecting elements so that the shield portion comes right over the gap between each X-ray detecting element.

The structure of the mask 14 and the alignment thereof with the array of the X-ray detecting elements 6 provide the following features:

(1) Both the edges of each X-ray detecting element in the slice direction are shielded from incident X-rays.

(2) The edges of the X-ray detecting elements arranged in the channel direction are continuously shielded by shield portions.

(3) The X-ray detecting elements that adjoin to each other in the slice direction share a shield portion.

Owing to the features (1) and (2), although that central portion of each X-ray detecting element which corresponds to the effective area of the corresponding photodiode is exposed to X-rays, the edges of the X-ray detecting element is little exposed. Thus, the sensitivity instability of the edges of the X-ray detecting elements does not hinder the sensitivity instability of the X-ray detecting elements. Owing to the feature (3), the arrangement error of X-ray detecting element modules can be canceled out.

Figure 6:
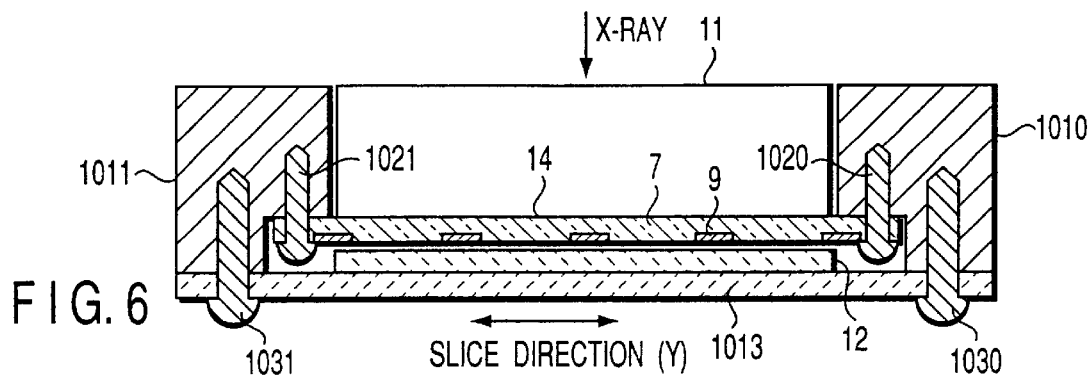
FIG. 6 is a sectional view showing the X-ray detector of FIG. 3, in greater detail.
Figure 7A:
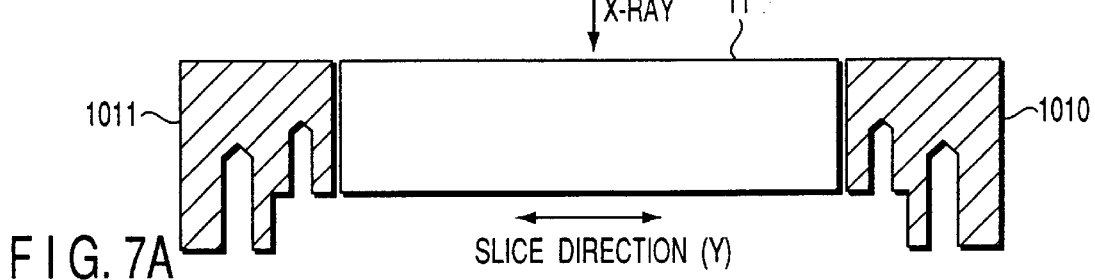
FIGS. 7A to 7C are sectional view, explaining the method of assembling the X-ray detector shown in FIG. 6.
Figure 7B:
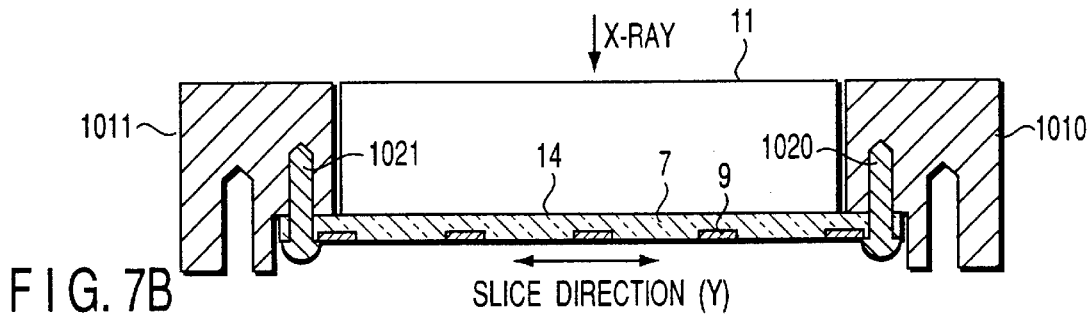
Figure 7C:
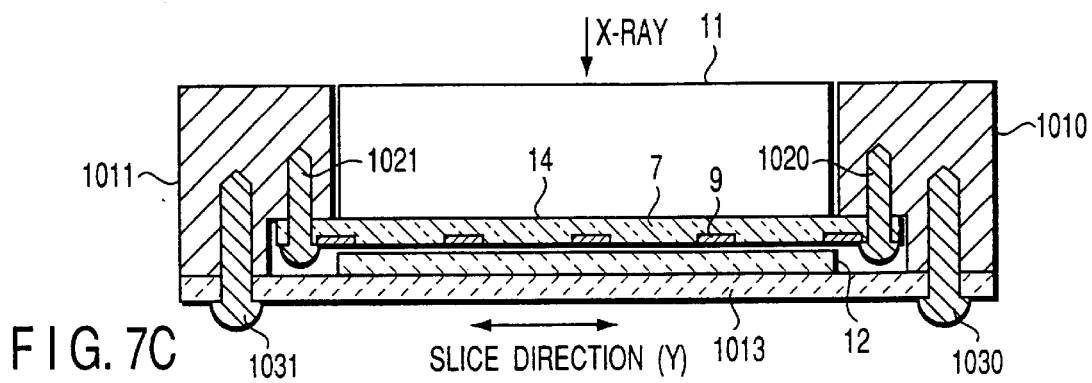

FIG. 6 is a sectional view that shows the X-ray detector 5. FIGS. 7A to 7C are sectional views explaining the method of assembling the X-ray detector 5. As seen from FIGS. 6, 7A to 7C, the collimator has arcuate supports 1010 and 1011 and plurality of collimator plates 11. Each arcuate support has a plurality of grooves.

As shown in FIG. 7A, the collimator plates 11 are fitted, at one end, in the grooves of the support 1010 and, at the other end, in the grooves of the support 1011. Then, as shown in FIG. 7B, the mask 14 is arranged at the back of the collimator 11 and secured to the supports 1010 and 1011 by means of screws 1020 and 1021. As shown in FIG. 7C, a ceramic substrate 1013 that has the photodiodes 13 on it is arranged at the back of the mask 14 and secured to the collimator supports 1010 and 1011 by means of screws 1030 and 1031. It should be noted that the scintillators 12 are mounted on the surface of the ceramic substrate 1013.

Since the mask 14 and ceramic substrate 1013 are mounted on the collimator supports 1010 and 1011, the X-ray detector 5 can be assembled with higher precision than in the case the mask 14 is mounted on the ceramic substrate 1013. This is because the collimator supports 1010 and 1011 have been made by machining or molding to high precision and posses high form stability. It is therefore possible to greatly reduce the distance between the mask 14 and each scintillator 12 mounted on the ceramic substrate 1013. The distance is provided to allow the arrangement error of the mask 14 and/or substrate 1013. Thus, the mask 14 can be positioned very close to the scintillators 12.

Figure 7D:
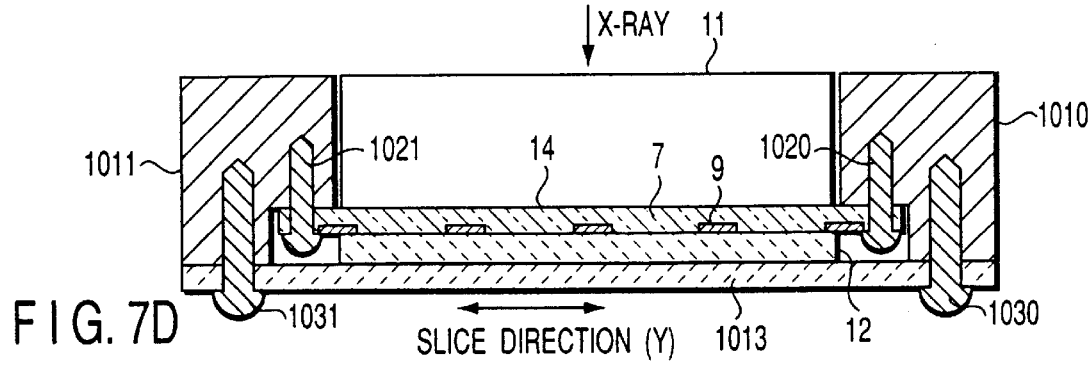
FIG. 7D is sectional view showing the modified X-ray detector.
Figure 9A:
FIGS. 9A through 9E are exterior views of variations of the mask of the present invention.
Figure 9B:
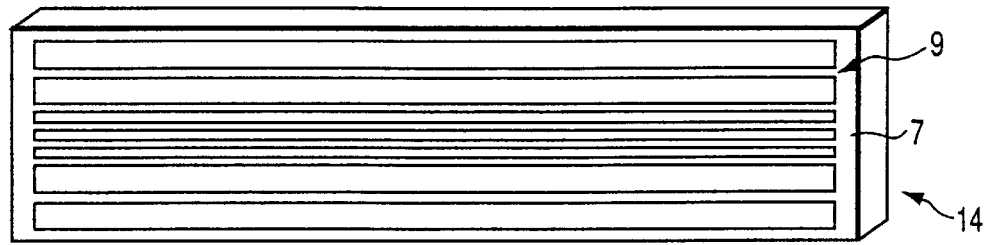
Figure 9C:
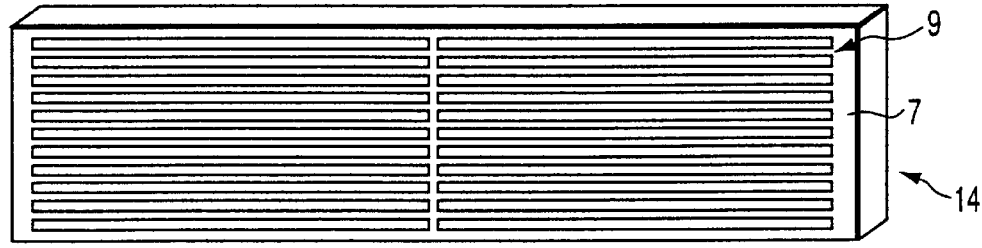
Figure 9D:
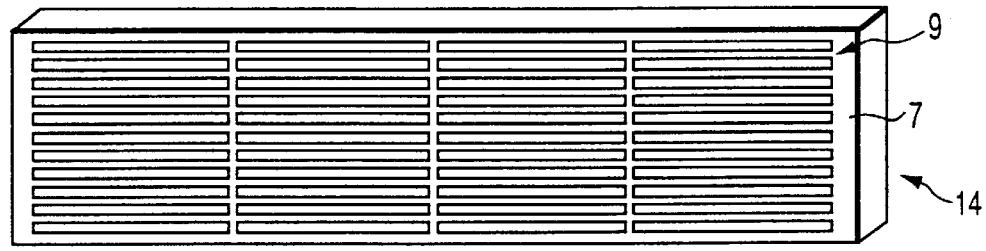
Figure 9E:
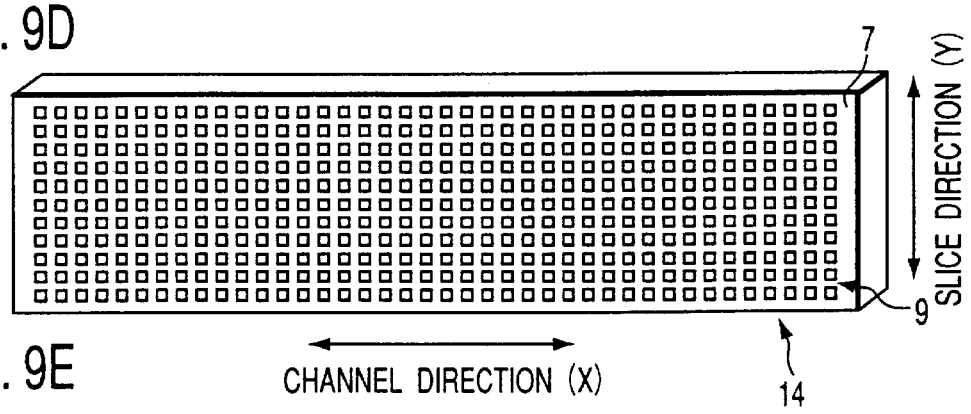

The mask 14 is placed on or above the scintillators 12, as showing FIG. 6 or FIG. 7D.

In the present embodiment, although the X-ray tube 1 and the two-dimensional X-ray detector 5 are mounted to the same ring, they may each be mounted to a separate ring. Moreover, although the X-ray detecting elements are arranged in the shape of a circular arc in the channel direction, this is not restrictive. The elements may be arranged in the form of a plane. Naturally, the number of the X-ray detecting elements arranged in the slice direction (corresponding to the number of slices) can be varied according to the purpose of use. Furthermore, there is no need to make all the X-ray detecting elements identical in size. The two-dimensional X-ray detector of the present invention that comprises multiple rows of X-ray detecting elements may be configured such that the size of X-ray detecting elements varies from row to row or some rows differ in the size of X-ray detecting element from the other rows. For example, an example is a non-uniform-pitch two-dimensional X-ray detector in which, in rows of X-ray detecting elements arranged in the slice direction, the closer the row is to the center, the smaller the dimension of the X-ray detecting element in the slice direction is (see Japanese Unexamined Patent Publication No. 10-24031).

Although the mask 14 has been described as having the shield portions 9 and the transparent portion 7, it may consist of shield portions alone. In this case, an example of the mask 14 would be a shielding plate having a pattern of holes corresponding to transparent portions. The transparent portion need not be a plate that is equal in shape and size to the array of the X-ray detecting elements but may be formed from transparent bars, two of which support both ends of each shield portion.

Next, the mask 14 will be described in detail. The transparent portion 7 is formed from a material that is substantially transparent to X-rays, i.e., a material having a very small X-ray absorption coefficient. Such materials include materials that are good in ease of processing and resistance to radiation, for example, polyethylene terephthalate (PET), acrylic resins, polyimide resins, epoxy resins, composites of these resins, and fiber-reinforced resins obtained by reinforcing these resins with carbon fiber or glass fiber. When the transparent portion is made of a material that is highly transparent to visible light, the array of X-ray detecting elements can be confirmed visually through the transparent portion, thus allowing for ease in alignment between the mask 14 and the X-ray detecting elements 6.

The shield portions 9 are formed from a material that has such a high X-ray absorption coefficient that X-rays are little or not at all allowed to pass through. X-ray absorption materials suitable for the shield portions include heavy metals, such as lead, tungsten, molybdenum, etc., sintered bodies of alloys of such heavy metals, powders of heavy metals or their alloys, and resins which contain powders of heavy metals sufficiently and uniformly. The shield portions may be formed from a wire made of a heavy metal such as lead, tungsten, or molybdenum.

Next, how to manufacture the shield portions 9 and the transparent portion 7 will be described.

First, the method of manufacturing the transparent portion will be described. A resin is formed into a desired shape and dimensions by a general technique, for example, a metal mold forming technique. As described above, the mask 14 has the shape of a circular arc in correspondence with the shape of the X-ray detecting element array. The shape may be imparted to the mask 14 by making the mask 14 arcuate from the beginning. Alternatively, the mask 14 may first shaped like a plate and may then be bent or deformed into an acruate mask.

Next, the molded transparent portion 7 is formed with grooves into which shield portions are to be fit. The grooves can be formed by grinding the transparent portion using a whetstone. Alternatively, in the case where the transparent portion is formed using a metal mold, grooves can be formed simultaneously with the transparent portion by previously providing the metal mold with heights corresponding to the grooves. However, the processing of grooves requires high precision. It is often required that grooves be formed in uniform dimensions over a distance of about 1 m in a very hard transparent portion made of GFRP by way of example or a metal mold. Thus, the manufacture of the transparent portion 7 in the present invention requires highly sophisticated molding techniques. To avoid the processing of long grooves, shield portions each consisting of a wire stretched linearly using clamps can be put on a transparent portion molded into the form of a plate and then glued to the transparent portion. Alternatively, transparent portions short in the channel direction and formed with grooves can be put on parts of shield portions from above and below so as to sandwich them and then glued to the shield portions.

The shield portions 9, each in the form of a wire made of an X-ray absorption material, are fit into grooves formed in the transparent portion 7. Alternatively, a resin adhesive that contains a proper amount of powder (say, about 1 micrometer in diameter) of an X-ray absorption material uniformly, for example, an epoxy adhesive, may be put into the grooves in the transparent portion and then hardened to thereby produce the shield portions. Alternatively, the shield portions may be produced by filling the grooves in the transparent portion with a proper amount of powder of an X-ray absorption material and then covering the grooves with an adhesive tape so that the powder is sealed in. Where the powder of an X-ray absorption material is sealed in, to prevent the powder from leaking the grooves may be formed so that they are not open at their both ends in the channel direction. If, on the other hand, the grooves are formed open at their both ends, then the open ends should be stopped with a resin adhesive or adhesive tape.

The wire made of an X-ray absorption material may be produced by rolling that material or by molding a resin that contains uniformly the powder of an X-ray absorption material into the form of a wire and then hardening it. The wire can be produced by preparing a plurality of wires in rectangular or circular in cross-section, stacking them one above another, and gluing them together with a resin that contains the powder of an X-ray absorption material uniformly or does not. The wire thus produced can be formed with the same dimensions as the grooves in the transparent portion and then fit into the grooves without any gap. If the wire is fit into the grooves with gaps, then the gaps may be filled with a resin that contains a heavy metal or its powder uniformly or does not. The gaps may be filled with a molten heavy metal or its alloy provided that it does not have thermal effects on the transparent portion 7 and the grooves.

At this point, if the shield portions are formed by fitting a plurality of wires into the grooves in the transparent portion, a plurality of shield portions of different aspect ratios can be produced readily by changing the number and shape of the wires.

Figure 8A:
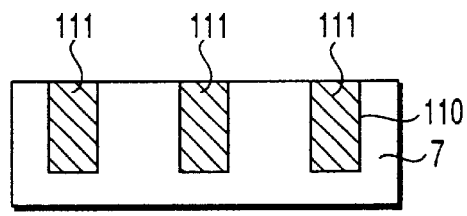
FIGS. 8A through 8D are cross-sectional views of the shield portions of the mask of the present invention.
Figure 8B:
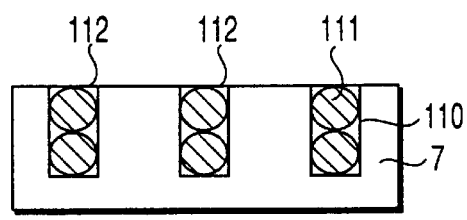
Figure 8C:
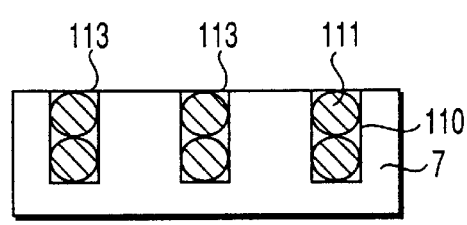
Figure 8D:
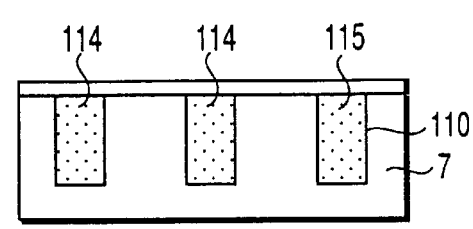

FIGS. 8A through 8D are cross-sectional views of the mask 14 manufactured according to the above-described methods. In FIG. 8A, there is illustrated the mask 14 produced by fitting wires 111 of the same shape and dimensions as grooves 10 of the transparent portion 7 into those grooves. FIG. 8B shows the mask that is produced by fitting wires 111 circular in cross-section into the grooves 110 and filling gaps within the grooves with a resin 112 that does not contain the powder of an X-ray absorption material. FIG. 8C shows the mask that is produced by fitting wires 111 circular in cross-section into the grooves 110 and filling gaps within the grooves with a resin 13 that contains the powder of an X-ray absorption material. FIG. 8D shows a mask produced by filling grooves 110 with the powder of an X-ray absorption material 114 and covering the open ends of the grooves with an adhesive sheet 115.

In addition, the mask 14 may also be produced as shown in FIGS. 9A through 9D by cutting the pattern of the transparent portion 7 from a thin plate that contains a heavy metal or its alloy and is less than 1 mm in thickness by means of etching, wire discharging, punching, or laser processing.

Such a mask is placed above the array of the X-ray detecting elements 6 by screwing, screwing with positioning pin, or bonding.

Next, the shape and dimensions of the shield portions 9 will be described.

The shield portions has a length equal to the overall length of the X-ray detecting element array in the channel direction. As shown in FIG. 10, in order to keep a relatively high sensitivity and absorb arrangement error, the shield portion 9 has a width equal to or somewhat narrower than the interval between the effective areas of X-ray detecting elements that adjoin to each other in the slice direction. More specifically, the width of the shield portion is set at, for example, 2a+b+c, where a is the width of the edge of the X-ray detecting element, b is the maximum arrangement error, and c is the width of the gap between the elements 6 arranged side by side in the slice direction. In an actual example, the width a is 10 $\mu$m, the maximum arrangement error b is 100 $\mu$m, and the width c is 160 $\mu$m. The error b may be much greater than the width a and the width c such that 2b>2a+b+c. In this case, the shield portion 9 may be 2b as well.

Although the shield portions 9 have been described as being arranged at a given pitch along the slice direction, the X-ray detecting elements 6 may differ in size according to their position in the slice direction. In such a case, the shield portions are arranged at various pitches according to the varying sizes of the X-ray detecting elements. It is required for the shield portions 9 to cover the gap between each X-ray detecting element and the edges of the respective X-ray detecting elements in the slice direction with certainty by selecting the widths of the individual shield portions according to the X-ray sensitivity distribution of each detecting element that varies according to its dimension in the slice direction.

Depending on the image quality and cost conditions required with X-ray computerized tomography apparatus, it might be supposed to set the width of the shield portions a little narrower than the above-described width to thereby allow for the incidence of X-rays onto parts of the edges of the detecting elements. In such a case as well, the displacement of the X-ray detecting element modules in the slice direction that occurs in manufacturing the detector is virtually concealed by the shield portions of the invention and therefore the generation of artifacts can be suppressed to some degree.

It is desired that the height of the shield portions be kept as low as possible in contrast to the prior art technique. The reason is that an artifact that might occur when X-rays are prevented by the shield portions from falling on the effective areas of the detecting elements at the time of shifting the focus of X-rays can be circumvented and the mask used in the present invention is not intended to shield scattered X-rays. However, the higher the mask, the lower the X-ray absorption rate becomes. Thus, the height of the shield portions is to be determined according to the kind of an X-ray absorption material actually used. For example, when lead or tungsten is used as an X-ray absorption material, the height can be set to about 0.1 to 0.5 mm.

FIGS. 11A through 11E show various cross-sectional shapes of the shield portions 9. The shield portions are square, rectangular, semi-circular, semi-elliptical, or trapezoidal in cross-sectional shape. To suppress the generation of semi-shadows as much as possible, it is desired that the shield portions be semi-circular, semi-elliptical, or trapezoidal. Further, it is preferable for the shield portions to be thin semi-circular rather than semi-elliptical.

In the above description, the edges of all the X-ray detecting elements 6 are shielded by the shield portions 9. However, it might be unnecessary to shield the outermost X-ray detecting elements in the slice direction because the thickness of X-rays can be adjusted by the collimator.

The two-dimensional array of X-ray detector described so far is intended for use in an X-ray computerized tomography apparatus; however, this is not restrictive. The X-ray detector is adaptable to various apparatuses other than X-ray computerized tomography apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A two-dimensional array type of X-ray detector comprising:
   a two-dimensional array of X-ray detecting elements in X and Y directions for converting incident X-rays into electric signals; and
   line-shaped shielding members provided in the X-ray incidence side of said X-ray detecting elements, each of said line-shaped shielding members extending substantially parallel to the X direction, said shielding members being arranged in the Y direction, each of said shielding members shielding edges of those X-ray detecting elements arranged in the X direction from the incident X-rays.

2. The two-dimensional array of X-ray detector according to claim 1, wherein each of said shielding members shields the edges of paired X-ray detecting elements that adjoin to each other in the Y direction.

3. The two-dimensional array of X-ray detector according to claim 1, wherein each of said shielding members is rectangular, circular, semi-circular or trapezoidal in cross-sectional shape.

4. The two-dimensional array of X-ray detector according to claim 1, further comprising transparent members for supporting said shielding members so that they are arranged at a given pitch equal to the pitch of said X-ray detecting elements.

5. The two-dimensional array of X-ray detector according to claim 1, wherein said X-ray detecting elements have various dimensions in the Y direction and said transparent members supports said shielding members so that they are arranged at various pitches according to the dimensions of said X-ray detecting elements in the Y direction.

6. The two-dimensional array of X-ray detector according to claim 1, wherein each of said shielding members has a width substantially equal to the interval between effective areas of said X-ray detecting elements arranged in the Y direction.

7. The two-dimensional array of X-ray detector according to claim 1, wherein said shielding members are provided on or above said array of X-ray detecting elements.

8. A two-dimensional array type of X-ray detector comprising:
    a two-dimensional array of X-ray detecting elements in X and Y directions for converting incident X-rays into electric signals;
    line-shaped shielding members provided in the X-ray incidence side of said X-ray detecting elements, each of said shielding members extending substantially parallel to the X direction, said shielding members shielding edges of those X-ray detecting elements arranged in the X direction from the incident X-rays; and
    transparent members substantially transparent to X-rays for supporting said shielding members.

9. The two-dimensional array of X-ray detector according to claim 8, wherein said shielding members are provided on or above said array of X-ray detecting elements.

10. The two-dimensional array of X-ray detector according to claim 8, wherein each of said shielding members shields the edges of paired X-ray detecting elements that adjoin to each other in the Y direction.

11. The two-dimensional array of X-ray detector according to claim 8, wherein each of said shielding members is rectangular, circular, semi-circular or trapezoidal in cross-sectional shape.

12. The two-dimensional array of X-ray detector according to claim 8, wherein each of said transparent members formed from polyethylene terephthalate, acrylic resin, polyimide resin, epoxy resin, a composite of at least polyethylene terephthalate, acrylic resin, polyimide resin, and epoxy resin, fiber-reinforced polyethylene terephthalate, fiber reinforced acrylic resin, fiber-reinforced polyimide resin, fiber-reinforced epoxy resin, or a fiber-reinforced composite.

13. The two-dimensional array of X-ray detector according to claim 8, wherein said shielding members are fit into grooves formed in said transparent members.

14. The two-dimensional array of X-ray detector according to claim 8, wherein said shielding members are formed from a resin that contains the powder of a heavy metal.

15. The two-dimensional array of X-ray detector according to claim 8, wherein said shielding members are formed from a heavy metal and a resin that contains the powder of the heavy metal.

16. The two-dimensional array of X-ray detector according to claim 8, wherein said shielding members are formed from the powder of a heavy metal sealed in grooves formed in said transparent members.

17. The two-dimensional array of X-ray detector according to claim 8, wherein said shielding members are formed from lead, tungsten, molybdenum, or an alloy at least two component of which are selected from the group consisting of lead, tungsten, and molybdenum.

18. The two-dimensional array type of X-ray detector according to claim 8, wherein each of said shielding members is a wire made of lead, a wire made of tungsten, a wire made of molybdenum, or a wire made of an alloy at least two components of which are selected from the group consisting of lead, tungsten and molybdenum.

19. An X-ray computerized tomography apparatus comprising:
    an X-ray tube for directing X-rays toward a human body under examination;
    an X-ray detector for detecting X-rays passed through the human body; and
    a computer for producing tomography image data concerning at least one slice an the basis of the output of said X-ray detector,
    said X-ray detector comprising: X-ray detecting elements arranged in channel and slice directions for converting incident X-rays into electric signals; and line-shaped shielding members placed in the X-ray incidence side of said X-ray detecting elements; each of shielding members extending substantially parallel to the channel direction, said shielding members shielding edges of those X-ray detecting elements arranged in the channel direction from the incident X-rays.

20. An X-ray computerized tomography apparatus comprising:
    an X-ray tube for directing X-rays toward a human body under examination;
    an X-ray detector for detecting X-rays passed through the human body; and
    a computer for producing tomography image data concerning at least one slice on the basis of the output of said X-ray detector,
    said X-ray detector comprising: X-ray detecting elements arranged in channel and slice directions for converting incident X-rays into electric signals; line-shaped shielding members placed in the X-ray incidence side of said X-ray detecting elements, each of said shielding members extending substantially parallel to the channel direction, each of said shielding members shielding edges of those X-ray detecting elements arranged in the channel direction from the incident X-rays.

21. An X-ray computerized tomography apparatus comprising:
    an X-ray tube for directing X-rays toward a human body under examination;
    an X-ray detector for detecting X-rays passed through the human body; and
    a computer for producing tomography image data concerning at least one slice on the basis of an output of said X-ray detector,
    wherein said X-ray detector comprises: a collimator having a plurality of collimator plates and supports arranging the collimator plates in a channel direction; line-shaped shielding members mounted on said supports, located at a back of said collimator, and extending substantially parallel to the channel direction; transparent members being substantially transparent to X-rays and supporting said shielding members; a substrate mounted on said supports and located at a back of said shielding members; and a plurality of X-ray detecting elements arranged on the substrate in the channel direction and a slice direction such that those edges of the X-ray detecting elements which are arranged in the channel direction are shielded by said shielding members.

22. A method of assembling an X-ray detector of two-dimensional array type designed for use in an X-ray computerized tomography apparatus and comprising a collimator having a plurality of collimator plates, supports arranging the collimator plates in the channel direction, and a plurality of X-ray detecting elements, said method comprising the steps of:

mounting line-shaped shielding members on said supports at a back of said collimator, each of said shielding members extending substantially parallel to the channel direction, said shielding members being supported by transparent members being substantially transparent to X-rays; and mounting a substrate on said supports at a back of said shielding members, adjacent to said substrate there being arranged said X-ray detecting elements in the channel direction and a slice direction such that said shielding members shield those edges of said X-ray detecting elements which are arranged in the channel direction.

* * * * *